United States Patent
Kohno et al.

(10) Patent No.: US 10,071,042 B2
(45) Date of Patent: Sep. 11, 2018

(54) EXTERNAL DERMATOLOGICAL AGENT FOR ANTI-AGEING

(71) Applicant: Hayashibara Co., Ltd., Okayama-shi, Okayama (JP)

(72) Inventors: Keizo Kohno, Okayama (JP); Satomi Miyata, Okayama (JP); Toshiharu Hanaya, Okayama (JP); Shigeharu Fukuda, Okayama (JP)

(73) Assignee: HAYASHIBARA CO., LTD., Okayama (JP)

( * ) Notice: Subject to any disclaimer, the term of this patent is extended or adjusted under 35 U.S.C. 154(b) by 0 days.

(21) Appl. No.: 15/304,181

(22) PCT Filed: Apr. 13, 2015

(86) PCT No.: PCT/JP2015/061373
§ 371 (c)(1),
(2) Date: Oct. 14, 2016

(87) PCT Pub. No.: WO2015/159854
PCT Pub. Date: Oct. 22, 2015

(65) Prior Publication Data
US 2017/0035676 A1 Feb. 9, 2017

(30) Foreign Application Priority Data
Apr. 14, 2014 (JP) ................. 2014-082524

(51) Int. Cl.
| | |
|---|---|
| *A01N 43/04* | (2006.01) |
| *A61K 31/70* | (2006.01) |
| *A61K 8/60* | (2006.01) |
| *A61Q 19/02* | (2006.01) |
| *A61Q 19/08* | (2006.01) |
| *A61K 8/44* | (2006.01) |
| *A61K 31/7076* | (2006.01) |
| *A61K 31/706* | (2006.01) |
| *A61K 31/7064* | (2006.01) |

(52) U.S. Cl.
CPC ........... *A61K 8/606* (2013.01); *A61K 8/44* (2013.01); *A61Q 19/02* (2013.01); *A61Q 19/08* (2013.01); *A61K 31/706* (2013.01); *A61K 31/7064* (2013.01); *A61K 31/7076* (2013.01)

(58) Field of Classification Search
None
See application file for complete search history.

(56) References Cited

U.S. PATENT DOCUMENTS

| 9,301,962 | B2 | 4/2016 | Kohno et al. | |
|---|---|---|---|---|
| 2002/0042380 | A1* | 4/2002 | Castiel | A61K 8/676 514/24 |
| 2005/0250710 | A1 | 11/2005 | Wakamatsu et al. | |
| 2007/0248633 | A1 | 10/2007 | Baldo | |
| 2009/0041848 | A1 | 2/2009 | Aimi et al. | |
| 2009/0253794 | A1 | 10/2009 | Tomono et al. | |
| 2013/0165399 | A1* | 6/2013 | Kohno | A61K 31/7076 514/47 |

FOREIGN PATENT DOCUMENTS

| EP | 1547577 A1 | 6/2005 |
|---|---|---|
| EP | 2204154 A1 | 7/2010 |
| EP | 2583972 A1 | 4/2013 |
| EP | 2671565 A1 | 12/2013 |
| JP | 2007-291102 A | 11/2001 |
| JP | 2004-67576 A | 3/2004 |
| JP | 2004-91376 A | 3/2004 |
| JP | 2008-7411 A | 1/2008 |
| JP | 2008-169196 A | 7/2008 |
| JP | 2008-255020 A | 10/2008 |
| JP | 2008-260721 A | 10/2008 |
| JP | 2009-040690 A | 2/2009 |
| JP | 2009-249306 A | 10/2009 |
| JP | 2012-58557 A | 10/2009 |
| JP | 2011-032187 A | 2/2017 |
| WO | 2007/011066 A1 | 1/2007 |
| WO | 2011/158904 A | 12/2011 |

OTHER PUBLICATIONS

Bae et al. Food and Chemical Toxicolgy (2008), vol. 46, pp. 1298-1307.*
Farage et al., Textbook of aging skin, Springer, pp. 1-10 (2010).
Ogura et al., In vitro reconstruction of 3-D elastic fiber in a novel dermal equivalent, J. Soc. Cosmet. Chem. Jpn., 44(4):278-284 (2010).
Fisher et al., Collagen fragmentation promotes oxidative stress and elevates matrix metalloproteinase-1 in fibroblasts in aged human skin, The American Journal of Pthology, 174(1):101-114 (2009).

(Continued)

*Primary Examiner* — Patrick T Lewis
(74) *Attorney, Agent, or Firm* — Browdy and Neimark, PLLC

(57) ABSTRACT

The present invention aims to provide an external dermal composition for anti-ageing, which prevents or improves apparent skin problems such as age-related or senescent wrinkles, fine wrinkles, saggings, spots, etc., as well as maintaining or enhancing the skin barrier functions. The object is solved by providing an external dermal agent for anti-ageing, which contains as an effective ingredient(s) one or more members selected from the group consisting of adenosine N1-oxide 5'-phosphate, analogs thereof, and their salts.

5 Claims, No Drawings

(56) References Cited

OTHER PUBLICATIONS

Gilchrest et al., Mechanisms of ultraviolet light-induced pigmentation, Photochemistry and Photobiology, 63(1):1-10 (1995).
Abe, Fragrance Journal, pp. 88-95 (2005) with Excerpt English translation.
Search Report from EP application 15 780 618.3.

* cited by examiner

EXTERNAL DERMATOLOGICAL AGENT FOR ANTI-AGEING

TECHNICAL FIELD

The present invention relates to an external dermal agent for anti-ageing (may be abbreviated as "an anti-ageing external dermal agent", hereinafter), and particularly to an anti-ageing external dermal agent which contains as an effective ingredient(s) one or more of adenosine N1-oxide 5'-phosphates, analogs thereof, and their salts.

BACKGROUND ART

To keep youthfulness to the end of life is a common desire among all humankind, however, for a long time, humans could not have been spared from changes in their skin with ageing, such as wrinkles, fine wrinkles, saggings, and spots; there has been considered that the human skin or the skin also becomes senescent as we get older and becomes to show apparent changes such as wrinkles, fine wrinkles, saggings, and spots that are, so to speak, "natural providence" and inevitably unavoidable.

Recently, there has been gradually revealed the cause and function of apparent changes in the skin with ageing, such as wrinkles, fine wrinkles, saggings, and spots, as the progress of researches on the structure and the metabolic mechanism of the skin. As well known, the skin is constructed by the outer thin-layer of epidermis (epithelia) and the deeper thick-layer of dermis (connective tissue), wherein the epidermis as the outermost layer protects living bodies from the external world and prevents the exudation of the internal moisture and nutrients to the outside of human bodies; while, the dermis, as a connective tissue having a structure of multifunctionally/three-dimensionally extended fibroblasts, collagens, elastins, proteoglycans, etc., and plays a role in imparting strength, extensibility, or elasticity to the skin. It is also said that, as the reduction of sebum and moisture levels in the skin with ageing, the keratinous layer in the skin surface becomes susceptive to lose its moisture-retaining ability to easily induce fine wrinkles and rough skin due to dryness, etc.

The epidermis is constituted by "keratinous layer" (horny cell layer), "granulosa layer", "stratum spinosum", and "stratum germinativum" that are located in this order from the outer side of the skin, where keratinocytes generated in stratum germinativum sequentially move toward the outer side of the skin and mature into keratinous layer, and finally they are peeled off. In particular, keratinocytes proliferate in stratum germinativum existing in the innermost of the skin, and differentiate therein, and then move toward the upper layer of the skin and finally change into a keratinous layer existing in the outermost of the skin and then they are peeled off. These serial processes of keratinocyte proliferation, movement, differentiation, and peeling off are called turnover, wherein keratinocytes newly regenerate at a constant cycle to keep the homeostasis of the skin, however, it is said that the delaying of the turnover of the skin with ageing results in inducing wrinkles, saggings, and rough skin. The turnover rate of the skin varies depending on the part of the human body, however, it is roughly said to be about 20 days for the skin turnover of healthy teenagers, about 28 days for those in 20s, about 40 days for those in 30s, about 55 days for those in 40s as about two times longer than those in 20s, and about 75 days for those in 50s (see Non-Patent Literature 1).

As described above, since the delaying of turnover rate of the skin with ageing is said to induce wrinkles, saggings, and rough skins, even if such a delayed turnover with ageing could be recovered by any means to some extent, wrinkles, saggings, and rough skins can be effectively improved, though the turnover rate in what we call pre-ageing generations including those with ages at around 30 though around 50, who begin to be anxious about the abovementioned skin deteriorations, would hardly be shortened to the normal skin turnover rate of generations in 20s (see Patent Literature 1). From this point of view, turnover rate can be increased by accelerating at least any one of the serial steps of proliferation, movement, differentiation, and peeling off; however, any actual means for solving it has not yet been provided.

A keratinous layer is composed of numerous concentric layers of corneocytes, wherein a solid membrane composed of various proteins such as involucrin called cornified envelope for protecting subcellular site of corneocytes is present in the outermost layer of corneocytes. Such cornified envelope plays an important role in the barrier function of the skin. It is well known that, upon a reduction of the barrier function, ultraviolet (UV) ray, particularly, UV-A (longwave) that reaches the dermis will damage collagen, elastin, hyaluronic acid, etc.; and that, when the barrier function of the skin decreases, the skin is dried and decreased in its moisture-retaining ability, the oversecretion of sebum is induced, or the disorder of turnover is induced. The barrier function of the skin decreases with ageing, resulting in inducing wrinkles, fine wrinkles, saggings, and spots in the skin (see Patent Literatures 2 and 3).

The barrier function of the skin means the function of keratinous layer called the second barrier as referred to as the function of sebum membrane called the first barrier, i.e., the function for preventing both the invasion of external substances from the outside to the inside of living bodies and the release of excessive amount of moisture from the inside to the outside of living bodies; and means the function for separating the internal and the external region of living bodies with the structure of cell-cell adhesion called tight junction that exists in granular layer of epidermis adjacent to keratinous layer.

The reduction of fibroblasts and hyaluronic acid in dermis induced by ageing, as well as the cleavage of collagen and the denaturation of elastin, allegedly form wrinkles and lower the elasticity of the skin to induce saggings and rough skins. Since elastin, as fibra with a role of supporting collagen fibra, has a role of giving resiliency and elasticity to the skin (see Non-Patent Literature 2). Also, matrix metalloproteinase-1 for decomposing collagen is known to induce wrinkles (see Non-Patent Literature 3).

Endothelin-1, a substance for accelerating the activation and proliferation of melanocyte, is known as a cause of spots. Further, it is noted that pigmentation in the skin (spots) and skin dullness may be induced as a result of unsmooth evacuation of melanin, evacuated from melanocytes into epidermal cells, from epidermal cells (Non-Patent Literature 4).

Based on these research results and findings, there have been proposed a plurality of external dermal agents for reasonably preventing and/or improving apparent spots in the skin with ageing, such as wrinkles, fine wrinkles, saggings, and spots, i.e., external dermal agents for anti-ageing (see, for example, Patent Literatures 4 to 10); mankind are nearing to realize their desire to keep youthfulness to the end of the chapter step by step. The external dermal agents for anti-ageing proposed so far have been realized as a result of pursuing only a few possibilities from among many possibilities, and now still desired is to provide a novel external dermal agent for anti-ageing from more multiple different angles, including another different mechanism of exerting anti-ageing effect, improved handleability, and feasibility of production.

PRIOR ART LITERATURES

Patent Literatures

Patent Literature 1: Japanese Patent Kokai No. 2012-056857
Patent Literature 2: Japanese Patent Kokai No. 2004-091376
Patent Literature 3: Japanese Patent Kokai No. 2008-007411
Patent Literature 4: Domestic Re-Publication of PCT International Publication No. WO2007/011066
Patent Literature 5: Japanese Patent Kokai No. 2007-291102
Patent Literature 6: Japanese Patent Kokai No. 2008-169196
Patent Literature 7: Japanese Patent Kokai No. 2008-255020
Patent Literature 8: Japanese Patent Kokai No. 2008-260721
Patent Literature 9: Japanese Patent Kokai No. 2009-040690
Patent Literature 10: Japanese Patent Kokai No. 2009-249306

Non-Patent Literatures

Non-Patent Literature 1: "Textbook of Aging Skin", Farage et al., as editors, published by Springer, 2010
Non-Patent Literature 2: "Journal of Society of Cosmetic Chemists of Japan", Vol. 44, No. 4, pp. 278 to 284, 2010
Non-Patent Literature 3: "American Journal of Pathology", Fisher et al., Vol. 174, No. 1, pp. 101-114, 2009
Non-Patent Literature 4: "Photochemistry and Photobiology", Gilchrest et al., Vol. 63, No. 1, pp. 1 to 10, 1996

DISCLOSURE OF INVENTION

Object of the Invention

The present invention, which was made while taking the above conventional techniques into consideration, has an object to provide a novel external dermal agent for anti-ageing, which prevents or improves apparent changes with ageing, such as wrinkles, fine wrinkles, saggings, and spots in the skin.

Means to Attain the Object

The present inventors energetically, continuously made researches and efforts to solve the above object. As a result, they found the followings and accomplished the present invention: Adenosine N1-oxide 5'-phosphates, analogs thereof, and their salts exert an advantageous anti-ageing effect, i.e., they have actions of improving turnover, maintaining or enhancing the barrier function, enhancing the expression of filaggrin protein, accelerating the production of elastin, inhibiting the production of matrix metalloproteinase-1, or inhibiting the production of endothelin-1 in the skin; and prevent and improve the formation of wrinkles, fine wrinkles, saggings, and spots in the skin with ageing.

The present invention solves the above object by providing an external dermal agent for anti-ageing, which contains as an effective ingredient(s) one or more of adenosine N1-oxide 5'-phosphates, analogs thereof, and their salts.

The present inventors also found that the anti-ageing effects of adenosine N1-oxide 5'-phosphates, analogs thereof, and their salts are significantly improved, when used in combination with ascorbic acid 2-glucoside, epigallocatechin gallate, and/or ethylenediaminetetraacetic acid (EDTA).

Effect of the Invention

The anti-ageing external dermal agent of the present invention improves the turnover, maintains or enhances the barrier function, enhances the expression of filaggrin protein, maintains or accelerate the production of elastin, inhibits the production of matrix metalloproteinase-1, or inhibits the production of endothelin-1 in the skin; and therefore the anti-ageing external dermal agent effectively prevents or improves the formation of wrinkles, fine wrinkles, saggings, and spots in the skin with ageing.

MODE FOR CARRYING OUT THE INVENTION

The anti-ageing external dermal agent of the present invention contains as an effective ingredient(s) any one or more of adenosine N1-oxide 5'-phosphates, analogs thereof, and their salts. Independently of origins, the above adenosine N1-oxide 5'-phosphates, analogs thereof, and their salts can be those which are purified from natural substances or those which are obtained through chemical synthesis. The term analogs of adenosine N1-oxide 5'-phosphate as referred to as in the present invention include, for example, adenosine N1 oxide, 3'-α-glucosyl adenosine N1-oxide, 5'-α-glucosyl adenosine N1-oxide, adenosine N1-oxide 5'-diphosphate, and adenosine N1-oxide 5'-triphosphate. The term "salts of adenosine N1-oxide 5'-phosphates" as referred to as in the present invention include, for example, sodium adenosine N1-oxide 5'-phosphate and potassium adenosine N1-oxide 5'-phosphate; among which, in terms of effects and functions, preferable are adenosine N1-oxide 5'-phosphates, 3'-α-glucosyl adenosine N1-oxide, and 5'-α-glucosyl adenosine N1-oxide; more preferable are adenosine N1-oxide 5'-phosphates, adenosine N1-oxide, and 3'-α-glucosyl adenosine N1-oxide; and furthermore preferable are adenosine N1-oxide 5'-phosphates and adenosine N1-oxide. Also, adenosine N1-oxide 5'-phosphates are superior to adenosine N1-oxide in photostability and solubility. Since salts of adenosine N1-oxide 5'-phosphates act as adenosine N1-oxide 5'-phosphates, adenosine N1-oxide 5'-phosphates and their salts exert substantially the same effects, however, the latter is superior to the former in solubility. Any of these compounds may contain components derived from production materials and by-products formed in the production processes, and usually they have a purity of at least 95% by mass, desirably at least 98% by mass, and more desirably at least 99% by mass ("% by mass" is abbreviated as "%" throughout the specification, unless specified otherwise).

The external dermal agent of the present invention is explained in detail hereinafter:

In the external dermal agent of the present invention, one or more of adenosine N1-oxide 5'-phosphates, analogs thereof, and their salts are usually incorporated into the total mass of the agent in a preferable percentage of 0.001 to 10.0%, and more preferably 0.01 to 1.0%; where, when the percentage is less than 0.001%, the above-identified ingredients could not sufficiently exert their desired effects; while, when it is over 10.0%, such desired-effects may not be attained in a dose dependent manner and such over-doses may not be recommendable.

The adenosine N1-oxide 5'-phosphates, analogs thereof, and their salts used in the present invention can be advantageously used alone because they exert in themselves a turnover-improving action, barrier-function-maintaining/accelerating action, elastin-production-maintaining/accelerating action, matrix-metalloproteinase-1-production-inhibitory action, and endothelin-1-production-inhibitory action in the skin; and they can be arbitrarily used in combination with other ingredients.

Since the anti-ageing effect of adenosine N1-oxide 5'-phosphates, analogs thereof, and their salts can be significantly improved when used in combination with ascorbic acid 2-glucoside, epigallocatechin gallate, and/or EDTA, these ascorbic acid 2-glucoside, epigallocatechin gallate, and EDTA can be advantageously used as ingredients for the anti-ageing external dermal agent of the present invention.

The term "improving turnover" means to maintain in healthy states the serial processes (or turnover) of the proliferation, movement, differentiation, and peeling off of epidermal cells (or keratinocytes), as the one for making up human epidermis, which are constructed by "keratinous layer" (horny cell layer), "granulosa layer", "stratum spinosum", and "stratum germinativum". Concretely speaking, the above term means to shorten the turnover cycle of the skin as it becomes longer with ageing.

The anti-ageing external dermal agent of the present invention sequentially accelerates the differentiation of keratinocytes, enhances the activity of transglutaminase, promotes the production of cornified envelope, and improves the skin turnover, followed by effectively preventing the formation of and improving the state of wrinkles, fine wrinkles, saggings, and spots in the skin with ageing. Also, since the anti-ageing external dermal agent of the present invention reinforces the function of tight junction in the skin and maintains or enhances the barrier function in the skin to suppress the skin's moisture release, it effectively prevents the formation of or improves the state of fine wrinkles or saggings in the skin with ageing. Further, the anti-ageing external dermal agent enhances the production of elastin that imparts skin resiliency or elasticity and suppresses the production of matrix metalloproteinase-1 responsible for inducing wrinkles, resulting in effective prevention or improvement of wrinkles and saggings. In addition, the agent of the present invention effectively prevents or improves spots as a result of suppressing the production of endotherin-1.

The anti-ageing external dermal agent of the present invention can be incorporated with any conventional ingredients, depending on the actual form of the agent. Usually, such external dermal agent can be used with any one or more ingredients used in conventional external dermal agents as long as they do not deteriorate the prescribed functions and effects of the present invention. Examples of such include oily ingredients, surfactants, antiseptics (or antimicrobials), flavors, skin-whitenings, moisturizers, thickeners, antioxidants, chelators, UV-ray absorbing/scattering agents, vitamins, amino acids, anti-inflammatories, blood-circulation-promoting agents, seaweed extracts, astringents, anti-wrinkle agents, cell activators, anti-retrogradation inhibitors, hair-restoring/growing agents, percutaneous absorption accelerators, water, alcohols, water-soluble polymers, pH-controlling agents, foaming agents, powders, additives for pharmaceuticals, quasi-drugs, and food products, and effective ingredients for pharmaceuticals and quasi-drugs. By using the above ingredients, the anti-ageing external dermal agent of the present invention can be produced in usual manner.

Concrete examples of the above-identified oily ingredients include vegetable oils and fats such as nut oils of *Macadamia integrifolia*, castor oils, olive oils, cocoa pod oils, camellia oils, palm oils, Japan waxes, jojoba oils, grape seed oil, and avocado oil; animal oils such as mink oil and egg-yolk oil; waxes such as bees wax, cetaceum, lanolin, carnauba wax, and candelilla wax; hydrocarbons such as petrolatum, squalane, microcrystalline wax, ceresin wax, paraffin wax, and petroleum; natural and synthetic fatty acids such as capric acid, myristic acid, palmitic acid, stearic acid, behenic acid, lanolin fatty acid, linolic acid, linolenic acid, lauric acid, myristic acid, oleic acid, and isostearic acid; natural and synthetic higher alcohols such as cetanol, stearyl alcohol, hexyldecanol, octyldodecanol, lauryl alcohol, capryl alcohol, myristyl alcohol, cetyl alcohol, cholesterol, and phytosterol; and esters such as isopropyl myristate, isopropyl palmitate, octyldodecyl myristate, octyldodecyl oleate, and cholesteryl oleate.

Examples of the above-identified surfactants include nonionic surfactants such as sorbitan monolaurate, sorbitan monopalmitate, sorbitan sesquioleate, sorbitan trioleate, polyoxyethylene (20) sorbitan monolaurate, polyoxyethylene sorbitan monostearate, polyethylene glycol monooleate, polyethylene glycol alkylate, polyoxyethylene alkyl ether, polyglycol diether, lauroyl diethanol amide, fatty acid isopropanol amide, maltitol hydroxy fatty acid ether, alkylated polysaccharides, alkyl glucosides, and sugar esters; nonionic surfactants such as hydrophilic glyceryl monostearate, glycerol monostearate (self-emulsifying), polyglyceryl monostearate, sorbitan monooleate, polyoxyethylene glycol monostearate, polyoxyethylene sorbitan monostearate, polyoxyethylene cetyl ether, polyoxyethylated bees wax, and polyoxyethylene hydrogenated castor oil; anionic surfactants such as sodium stearate, potassium palmitate, cetyl sodium sulfate, sodium lauryl sulfate, triethanolamine palmitate, polyoxyethylene sodium lauryl phosphate, sodium N-acyl-L-glutamate, sodium palmitate, sodium laurate, sodium laurylate, potassium lauryl sulfate, alkylsulfate triethanolamine ether, turkeyred oil, linear dodecylbenzene sulfate, polyoxyethylene hydrogenated castor oil maleate, and acyl methyl taurate; cationic surfactants such as stearyl dimethyl benzyl ammonium chloride, stearyl trimethyl benzyl ammonium chloride, benzalkonium chloride, and lauryl amine oxide; and ampholytic surfactants such as alkylaminoethylglycine chloride solution, and lecithin.

Examples of the above-identified antiseptics (antimicrobials) include benzoic acid and salts thereof, salicylic acid and salts thereof, sorbic acid and salts thereof, dehydroacetic acid and salts thereof, p-hydroxybenzonate including benzoic acid alkyl ester, 2,4,4'-trichloro-2'-hydroxydiphenyl ether, 3,4,4'-trichlorocarbanilide, hexachlorophene, benzalkonium chloride, phenoxyethanol, hinokitiol, resorcin, ethanol, 1,3-butylene glycol, and Kankohso 201 (or "PIONIN").

Examples of the above-identified flavor include benzaldehyde, benzyl benzoate, phenyl acetate, santalol, eugenol, lilial, lyral, linalool, 2-methyl-3-(4-methylphenyl)-propanal, musk ketone, cinnamaldehyde, belt fix, methyl ionone, geranyl formate, "ISO E SUPER (CAS No. 54464-57-2), γ-undecalactone, hexyl salicylate, cis-3-hexenyl salicylate, methyl dihydrojasmonate, tetrahydrofurfuryl 2-mercaptopropionate, "KOVANOL" (hydroxymethylpentylcyclohexenecarboxaldehyde), vanillin, ethylvanillin, geranium oil, penny royal oil, birch oil, and armoise oil.

Examples of the above-identified skin-whiteners include ascorbic acid, derivatives thereof, and their salts; alkoxy salicylic acids and salts thereof; hydroquinone and derivatives thereof such as hydroquinone glycosides; tranexamic acid, derivatives thereof, and their salts; derivatives of resorcin; kojic acid, derivatives thereof, and their salts;

ellagic acid, linoleic acid, and their salts; *Matricaria recutita* extract; Tetra hydro curcuminoids; indigo extracts; and others.

Examples of the above-identified humectants include polyalcohols such as erythritol, xylitol, sorbitol, maltitol, glycerin, propylene glycol, 1,3-butylene glycol, polyglycerin, polyethylene glycol, dipropylene glycol, 1,2-penthane diol, and isoprene glycol; saccharides such as glucose, maltose, trehalose, derivatives of trehalose, dextrins, cyclodextrins, cyclic tetrasaccharide having a structure of cyclo{→6)-α-D-glucopyranosyl-(1→3)-α-D-glucopyranosyl-(1→6)-α-D-glucopyranosyl-(1→3)-α-D-glucopyranosy(1→} disclosed in International Patent Publication No. WO 02/10361, cyclic tetrasaccharide having a structure of cyclo{→6)-α-D-glucopyranosyl-(1→4)-α-D-glucopyranosyl-(1→6)-α-D-glucopyranosyl-(1→4)-α-D-glucopyranosy(1→} disclosed in Japanese Patent Kokai No. 2005-95148; natural moisture ingredients such as amino acids, sodium lactate, sodium pyrrolidone carbonate; mucopolysaccharides such as glycogen, locust bean gum, xyloglucan, quince seed, carrageenan, pectin, mannan, curdlan, succinoglucan, galactan, dermatan sulfate, keratan sulfate, chondroitin, chondroitin sulfate, mucoitin sulfate, kerato sulfate, chitin, heparan sulfate, hyaluronic acid, and hydrolyzates thereof; proteins and peptides such as silk and collagen, and water-soluble high molecular substances such as hydrolyzates thereof, as well as salts thereof; silicons such as dimethylpolysiloxane and methylphenylsiloxane; and culture supernatants such as those of lactobacilli, bifid bacteria, etc.

Examples of the above-identified thickeners include natural high-molecular substances such as alginate sodium, xanthan gum, aluminum silicate, seed extract of *Cydonia oblonga*, gum arabic, hydroxyethyl guar gum, carboxymethyl guar gum, guar gum, dextran, tragacanth gum, starch, pullulan, chitin, chitosan, agar, and cellulose; semi-synthetic-high-molecular substances such as hydroxypropyl cellulose, methylhydroxypropyl cellulose, menthyl cellulose, carboxymethyl cellulose, hydroxyethyl cellulose, soluble starch, cationized cellulose, and carboxymethyl chitin; and synthetic-high-molecular substances such as carboxyvinyl polymer, polyvinyl alcohol, polyvinyl pyrrolidone, and vinyl alcohol/vinyl acetate copolymer.

Examples of the above-identified antioxidants include dibutylhydroxytoluene, butylated hydroxyanisole, propyl gallate, L-ascorbic acid, vitamin E, catechins, and flavonoids.

Examples of the above-identified chelates include disodium edetate, ethylenediaminetetraacetic acid, pyrophosphates, hexametaphosphates, citric acid, and gluconic acid.

Examples of the above-identified pH-controlling agents include sodium hydroxide, potassium hydroxide, triethanolamine, nitrilotriethanol, citric acid, sodium citrate, boric acid, borax, and potassium hydrogenphosphate.

Examples of the above-identified UV-absorbing agents include p-amino benzoic acid UV-absorbing agents, anthranilic acid UV-absorbing agents, salicylic acid UV-absorbing agents, cinnamic acid UV-absorbing agents, benzophenone UV-absorbing agents, saccharide type of UV-absorbents, 3-(4'-methylbenzylidene)-d-camphor, 3-benzylidene-d, 1-camphor, urocanic acid, urocanic acid ethyl ester, 2-phenyl-5-methylbenzoxazole, 2,2'-hydroxy-5-methylphenyl-benzotriazole, 2-(2'-hydroxy-5'-t-octylphenyl)benzotriazole, 2-(2'-hydroxy-5'-methylphenyl)benzotriazole, dibenzalazine, dianisoylmethan, 4-methoxy-4'-t-butyl-dibenzoilmethane, 5-(3,3-dimethyl-2-norbornylidene)-3-pentane-2-one, 2-hydroxy-4-methoxybenzophenone, octyldimethyl-paraaminobenzoate, ethylhexyl-p-methoxycinnamate, titanium oxide, kaolin, and talc.

Examples of the above-identified vitamins include vitamin A and derivatives thereof; vitamin B's such as vitamin $B_1$ and derivatives thereof, vitamin $B_2$ and derivatives thereof, vitamin $B_6$ hydrochloride, vitamin $B_6$ tripalmitate, vitamin $B_6$ dioctanoate, vitamin $B_{12}$, vitamin $B_{15}$ and derivatives thereof; ascorbic acid and derivatives thereof; vitamin E's such as α-tocopherol, β-tocopherol, γ-tocopherol, and vitamin E acetate; vitamin D's; vitamin H; pantothenic acid; pantethine; vitamin F; vitamin K; vitamin P and derivatives thereof; and vitamin U, ferulic acid, γ-oryzanol, α-lipoic acid, orotic acid, Coenzyme Q10 ($CoQ_{10}$), and derivatives thereof. Further, salts of the above-exemplified compounds can be used.

Examples of the above-identified amino acids include glycine, alanine, valine, leucine, isoleucine, serine, threonine, phenylalanine, tyrosine, asparagine, glutamine, taurine, tryptophan, cystine, cysteine, methionine, proline, hydroxyproline, asparaginic acid, glutamic acid, arginine, histidine, lysine, carnitine, citrulline, and derivatives thereof, as well as salts thereof.

The anti-ageing external dermal agent of the present invention should not specifically be restricted to specific forms, and it can be used in any forms of, for example, aqueous solution systems, solubilized systems, emulsion systems, powder dispersion systems, solid-stick systems, two-layer water-oil systems, three-layer water-oil-powder systems. The anti-ageing external dermal agent should not specifically be restricted to any actual forms of formulations and not be bound by the distinction of Pharmaceutical Affairs Act on pharmaceuticals, quasi-drugs, and cosmetics. The external dermal agent for anti-ageing of the present invention means a composition to be applied dermally or intraorally to the skin, lip, or scalp as a pharmaceutical, quasi-drug, or cosmetic; ointments, creams, milky lotions, lotions, essences, jellies, gels, packs, shampoos, rinses, hair treatments, masks, mascaras, eyeliners, hair restorers, lipsticks, lip glosses, foundations, rouges, eye shadows, powders, manicures, soaps, body soaps, bath salts, powdered dentifrices, moistened dentifrices, toothpastes, liquid dentifrices, medical dentifrices, cachous, cachou films, mouthwashes, and gargles.

The following experiments explain the present invention in more detail.

Experiment 1: Effect of Adenosine N1-Oxide 5'-Phosphate and Analogues Thereof on the Turnover of Normal Human Epidermal Keratinocytes A serial processes of the proliferation, movement, differentiation, and peeling off of keratinocytes is called turnover, where keratinocytes turn over at a prescribed cycle rate to maintain the skin homeostasis; however, the turnover becomes to delay with ageing, allegedly resulting in inducing wrinkles, saggings, and rough skins. Accordingly, it is considered that the turnover rate will increase when the differentiation of keratinocyte is induced, followed by the improvement of wrinkles, saggings, and rough skins. Therefore, the turnover accelerating actions of adenosine N1-oxide 5'-phosphate and analogues thereof were evaluated with indexes of the differentiation-inducing action, cornified-envelope-production-accelerating action, and transglutaminase-activity-enhancing action by keratinocytes. This experiment was conducted in accordance with Hasegawa et al., "*Lipids*", Vol. 46, No. 6, pp. 529-535, 2011; and Sturniol et al., "*The Journal of Biological Chemistry*", Vol. 278, No. 48, pp. 48,066 to 48,073, 2003.

Experiment 1-1: Effect on the Differentiation of Keratinocytes

To 12-well plates, one milliliter of a cell suspension with a cell density of $2.5 \times 10^4$ cells/mL prepared by suspending normal human epidermal keratinocytes in EpiLife, a product name of a medium for keratinocytes containing a growth factor, commercialized by Life Technologies, Inc., 9800 Medical Center Drive Rockville, Md. 20850 USA; followed by culturing the cells until prevailing up to about ½ of the bottom surface of each well. Thereafter, the culture medium in each well was replaced with a medium for keratinocytes free of growth factor and cultured for two days, and then replaced with a fresh medium for keratinocytes, which contained any one of the test substances in Table 1 at respective concentrations as indicated in the table, and then cultured for three days. As a control, a culture system was provided similarly as above except for not adding any of the test substances. Under a microscopic condition, cell morphology was observed and evaluated for the keratinocyte-differentiation-inducing ability based on the following criteria:
Score 0: Unchanged
Score 1: The number of cells in a flattened form against the total cells is 50% or lower.
Score 2: The number of cells in a flattened form against the total cells is 50% or more.
Score 3: Nearly all of the cells are in an irregular shape and there appears some cells with gloss.

It means that the higher the score the more the cell differentiation was accelerated. Each experiment system was performed in a triplicate manner, followed by calculating a mean value for each system. Table 1 shows the action of adenosine N1-oxide 5'-phosphate analogues on differentiation induction of keratinocytes.

TABLE 1

| Test substance | | Score |
|---|---|---|
| Control | | 0.0 |
| Sodium adenosine N1-oxide 5'-phosphate | 10 μM | 2.0 |
| | 20 μM | 3.0 |
| | 40 μM | 3.0 |
| Adenosine N1-oxide | 10 μM | 2.0 |
| | 20 μM | 3.0 |
| | 40 μM | 3.0 |
| 3'-α-Glucosyladenosine N1-oxide | 40 μM | 2.0 |
| | 80 μM | 2.0 |
| | 160 μM | 3.0 |
| 5'-α-Glucosyladenosine N1-oxide | 200 μM | 2.0 |
| | 400 μM | 2.0 |
| | 800 μM | 3.0 |
| Adenosine | 100 μM | 0.0 |
| | 200 μM | 0.0 |
| | 400 μM | 0.0 |
| 3'-α-Glucosyladenosine | 200 μM | 0.0 |
| | 400 μM | 0.0 |
| | 800 μM | 0.0 |
| 5'-α-Glucosyladenosine | 200 μM | 0.0 |
| | 400 μM | 0.0 |
| | 800 μM | 0.0 |

As clear from Table 1, there was found no morphological change in normal human epidermal keratinocytes in Control with no addition of any test substance, while the experiment system with sodium adenosine N1-oxide 5'-phosphate or adenosine N1-oxide gave a morphological cellular change at a concentration of 10 μM and made cells with a flattened shape into smaller-sized ones after denucleation at a concentration of 20 to 40 μM, whereby the cells were changed to show irregular morphological shapes and some of which became to have a gloss, meaning that the cells' differentiation was accelerated. The systems with 3'-α-glucosyladenosine or 5'-α-glucosyladenosine gave a morphological change at respective concentrations of 40 to 80 and 200 to 400 μM, and made cells with a flattened shape into smaller-sized ones after denucleation at concentrations of 160 and 800 μM, whereby the cells were changed to show irregular morphological shapes and some of which became to have a gloss, meaning that the cells' differentiation was accelerated. While, adenosine at a concentration of 400 μM and 3'-α-glucosyladenosine or 5'-α-glucosyladenosine even at a concentration of 800 μM gave no morphological cellular change.

Within the range of concentrations tested, the differentiation of keratinocytes was accelerated by any one of sodium adenosine N1-oxide 5'-phosphate, adenosine N1-oxide, 3'-α-glucosyladenosine N1-oxide, and 5'-α-glucosyladenosine N1-oxide, among which sodium adenosine N1-oxide 5'-phosphate and adenosine N1-oxide were revealed to have a stronger effect. These results show that adenosine N1-oxide 5'-phosphates, analogues thereof, and their salts are effective as a turnover-improving agent because of their acceleration of the differentiation of keratinocytes.

Experiment 1-2: Effect on the Production Level of Cornified Envelope

Cornified envelope plays an important role in the barrier function in the skin. Wrinkles, fine wrinkles, saggings, and spots in the skin are induced by the reduction of the barrier function in the skin. Accordingly, the effect of adenosine N1-oxide 5'-phosphates and analogues thereof on the formation of cornified envelope were examined in this experiment, which was conducted in accordance with Hasegawa et al., "*Lipids*", Vol. 46, No. 6, pp. 529 to 535, 2011.

Normal human epidermal keratinocytes were cultured similarly as in Experiment 1-1, except for adding the test substances listed in Table 2 at prescribed concentrations to the cells. The resulting cultured cells were washed once with phosphate buffered saline (PBS), followed by scrapping off the cells adhered to each culture plate by adding 0.5 mL of PBS to each well of the plates. The cell suspensions thus obtained were added with 10% sodium lauryl sulfate solution in a volume of ¼ of each of the suspension volumes, followed by stirring and freezing the resulting mixtures at −80° C. After thawing, the resulting mixtures were centrifuged at 12,000×g for 15 min, followed by collecting the cell precipitates which were then washed once with phosphate buffered saline containing 2% sodium lauryl sulfate. The resulting mixtures were centrifuged at 12,000×g for 15 min, followed by collecting the cells and suspending the collected cells with phosphate buffered saline containing 2% sodium lauryl sulfate and 20 mM dithiothreitol. The resulting cell suspensions were boiled in a boiling water bath for one hour and measured for absorbance at a wavelength of 310 nm to determine the production level of cornified envelope for each test system added with any of the test substances. A control system was provided similarly as above except for not adding any one of the test substances to the system, and determined for absorbance at a wavelength of 310 nm similarly as in the above to be regarded as 100%. The production level of cornified envelope for each test substance was relatively evaluated based on the following equation.

Equation: Production level of cornified envelope (Relative value (%))=[(Absorbance of a sample with any one of test substances)/(Absorbance of Control)]×100

The experiment was repeated three times, and the data was subjected to the Dunnett's multiple comparisons with Control. The symbol "*" means a level of significance of p<0.01. Table 2 shows the action of analogues of adenosine N1-oxide 5'-phosphate on the production of cornified envelope associated with the differentiation of keratinocytes.

TABLE 2

| Test substance | | Production level (%) of cornified envelope |
|---|---|---|
| Control | | 100.0 |
| Sodium adenosine N1-oxide 5'-phosphate | 25 μM | 178.7* |
| Adenosine N1-oxide | 25 μM | 178.7* |
| 3'-α-Glucosyl adenosine N1-oxide | 200 μM | 141.4* |
| 5'-α-Glucosyl adenosine N1-oxide | 600 μM | 148.8* |
| Adenosine | 400 μM | 101.7 |
| Adenosine 5'-phosphate | 400 μM | 136.5 |
| 3'-α-Glucosyl adenosine | 800 μM | 104.2 |

As clear from Table 2, compared to Control with no addition of any of the test substances, the system with adenosine N1-oxide 5'-phosphate or adenosine N-1 oxide improved up to give a cornified-envelope-production level of about 180% at a concentration of 25 μM, revealing that they showed a significant action of enhancing the production of cornified envelope. While the system with 3'-α-glucosyl adenosine N1-oxide gave a significant action of enhancing the production of cornified envelope at a concentration of 200 μM. The system with 5'-α-glucosyl adenosine N1-oxide gave a significant action of enhancing the production of cornified envelope at a concentration of 600 μM. While, the system with adenosine 5'-phosphate tended to enhance the production of cornified envelope at a concentration of 400 μM. While, the system with adenosine or 3'-α-glucosyl adenosine showed no action of enhancing the production of cornified envelope even at concentrations of 400 μM and 800 μM, respectively.

Within the range of concentrations tested, production enhancements of cornified envelope were observed with sodium adenosine N1-oxide 5'-phosphate, adenosine N1-oxide, 3'-α-glucosyl N1-oxide, and 5'-α-glucosyl adenosine N1-oxide, wherein the effects of adenosine N1-oxide, sodium adenosine N1-oxide 5'-phosphate, and 3'-α-glucosyladenosine N1-oxide were revealed to be stronger, among which adenosine N1-oxide and sodium adenosine N1-oxide 5'-phosphate were revealed to be the strongest ingredients. These results indicate that adenosine N1-oxide 5'-phosphate, analogues thereof, and their salts are useful as turnover-improving agents depending on their production enhancements of cornified envelope.

Experiment 1-3: Effect on Transglutaminase Activity

Transglutaminase is an enzyme that catalyzes the cross-linkage of proteins and relates to the formation of cornified envelope; the enhancement of transglutaminase activity promotes the formation of cornified envelope and prevents or improves, for example, wrinkles, fine wrinkles, saggings, and spots in the skin. Therefore, the effect of adenosine N1-oxide 5'-phosphate and analogues thereof on the activity of transglutaminase was examined in this experiment in accordance with Sturniolo et al., "The Journal of Biological Chemistry", Vol. 278, No. 48, pp. 48,066 to 48,073, 2003.

Normal human epidermal keratinocytes were cultured similarly as in Experiment 1-1, except for adding the test substances as listed in Table 3 to respective culture systems. The cultured normal human epidermal keratinocytes were added with 100 μM of fluorescein cadaverine and allowed to stand for four hours. Thereafter, the resulting cells were washed once with phosphate buffered saline and further treated with cold methanol for 10 min for cell fixation. The fixed cells were washed thrice with cold methanol, followed by the addition of phosphate buffered saline. Fluorescein cadaverine taken in the cells via transglutaminase was analyzed with Cell Imaging Station, commercialized by Molecular Probes Life Technology, France, and the analyzed fluorescent intensities were regarded as transglutaminase activities. There was provided a control system similarly as in the above, except for not adding any of the test substances. The transglutaminase activity of each test substance was evaluated as a relative value determined with the following equation using the fluorescent intensity of the control system being regarded as 100%.

Equation: Transglutaminase activity (relative value (%))=[(Fluorescent intensity of a sample with any one of test substances)/(Fluorescent intensity of control)]×100

The experiment was repeated three times, and the data was subjected to the Dunnett's multiple comparisons with Control. The symbol "*" means a level of significance of p<0.01. Table 3 shows the action of analogues of adenosine N1-oxide 5'-phosphate on the activity of transglutaminase relating to the production of cornified envelope.

TABLE 3

| Test substance | | Transglutaminase activity (%) |
|---|---|---|
| Control | | 100 |
| Sodium adenosine N1-oxide 5'-phosphate | 20 μM | 569* |
| Adenosine N1-oxide | 20 μM | 632* |
| 3'-α-Glucosyl adenosine N1-oxide | 100 μM | 300 |
| 5'-α-Glucosyl adenosine N1-oxide | 400 μM | 404* |
| Adenosine | 400 μM | 360 |
| Adenosine 5'-phosphate | 400 μM | 244 |
| 3'-α-Glucosyl adenosine | 400 μM | 269 |
| 5'-α-Glucosyl adenosine | 400 μM | 33 |

As clear from Table 3, compared to a control system with no addition of any test substance, test systems with sodium adenosine N1-oxide 5'-phosphate and with adenosine N1-oxide at respective concentrations of 20 μM marked improved transglutaminase activities of up to about 570% and about 630%, respectively, and gave significant enhancement actions of transglutaminase activities. 5'-α-Glucosyladenosine N1-oxide showed a significant enhancement action on transglutaminase activity at a concentration of 400 μM. While, 3'-α-glucosyladenosine N1-oxide showed no significant enhancement action on transglutaminase activity at a concentration of 100 μM; however, it may be effective when used at a higher concentration, based on the effectiveness of 5'-α-glucosyladenosine N1-oxide at a concentration of 400 μM. While, adenosine, adenosine 5'-phosphate, 3'-α-glucosyladenosine, and 5'-α-glucosyladenosine showed no enhancement action on transglutaminase activity at a concentration of 400 μM.

It was revealed that the enhancement of transglutaminase activity was observed for sodium adenosine N1-oxide 5'-phosphate, adenosine N1-oxide, and 5'-α-glucosyladenosine N1-oxide, among which adenosine N1-oxide and sodium adenosine N1-oxide 5'-phosphate are greater than the others. These results indicate that adenosine N1-oxide 5'-phosphate, analogues thereof, and their salts have an enhancement action on transglutaminase activity and effectively act as a turnover-improving agent.

Experiment 2: Effect of the Enhancement Action of Adenosine N1-Oxide 5'-Phosphate and Analogues Thereof on the Tight-Junction Function of Cells Deriving from Human Epidermal-Like Cancer Cells Tight junction has a function of preventing the invasion of foreign substances from outside of living bodies to the inside and an excessive amount of moisture release from inside of the body to the outside. Therefore, the strengthening of tight junction would result in the skin miniaturization and the promotion of skin-barrier function. From these, this experiment is to examine the effect of adenosine N1-oxide 5'-phosphate and analogues thereof on tight junction, and it is demonstrated in accordance with Suzuki and Hara, "*Journal of Nutrition*", Vol. 139, No. 5, pp. 965 to 974, 2009.

A human epidermoid carcinoma cell line A-431 was suspended in a media, supplemented with any of the test substances disclosed in Table 4 and having respective concentrations as indicated in the table, to give a cell concentration of $1 \times 10^5$ cells/mL, and each cell suspension was placed in an insert cup for a 12-well culture plate by two milliliters per well, followed by culturing the cells until reaching a confluent state through over the bottom surface of each well. The inner and the outer cup volumes were adjusted to give two milliliters while checking both the liquid levels of the cups were constant, and lucifer yellow as a model for permeating substance, commercialized by Life Technologies Corporation, CA, USA, was added to each inner cup to give a final concentration of 100 μM. Thereafter, the fluorescent intensities of lucifer yellow in the culture media in both the inner and the outer cups were measured, followed by calculating the percentage of the fluorescent intensity of the outer cup against that of the sum of the outer and the inner cups for use as a transmittance of lucifer yellow with the following equation.

Equation: Transmittance of lucifer yellow (%)={(Absorbance of a liquid outside of an insert cup)/[(Absorbance of a liquid inside of the insert cup)+(Absorbance of the liquid outside of the insert cup)]}×100

There was provided a control system prepared similarly as above except for not adding any of the test substances, and the transmittance of lucifer yellow was regarded as 100% for evaluating the reduction of transmittance due to the reinforcement of the function of tight junction, based on the following equation.

Equation: Relative transmittance (Relative percentage (%)) of lucifer yellow=[(Transmittance of a sample with any one of test substances)/(Transmittance of control)]×100

The experiment was repeated three times, and the data was subjected to the Dunnett's multiple comparisons with control. The symbol "*" means a level of significance of p<0.01. Table 4 shows the action of analogues of adenosine N1-oxide 5'-phosphate on the tight junction of human epidermoid carcinoma cell.

TABLE 4

| Test substance | | Relative transmittance of lucifer yellow (%) |
|---|---|---|
| Control | | 100 |
| Sodium adenosine N1-oxide 5'-phosphate | 10 μM | 78.4 |
| | 20 μM | 62.3* |
| Adenosine N1-oxide | 10 μM | 71.6* |
| | 20 μM | 71.3* |
| 3'-α-Glucosyl adenosine N1-oxide | 200 μM | 112.3 |
| | 400 μM | 102.3 |
| 5'-α-Glucosyl adenosine N1-oxide | 200 μM | 97.1 |
| | 400 μM | 96.8 |
| Adenosine | 200 μM | 77.1* |
| | 400 μM | 67.4* |
| Adenosine 5'-phosphate | 200 μM | 90.6 |
| | 400 μM | 81.6 |
| 3'-α-Glucosyl adenosine | 200 μM | 94.5 |
| | 400 μM | 94.8 |
| 5'-α-Glucosyl adenosine | 200 μM | 94.2 |
| | 400 μM | 82.3 |

As clear from Table 4, compared to a control system with no addition of any test substance, the test system with sodium adenosine N1-oxide 5'-phosphate marked about 60% reduction of lucifer yellow transmittance at a concentration of 20 μM, revealing that it has a significant action of enhancing the function of tight junction. Adenosine N1-oxide was revealed to have a significant action of enhancing the function of tight junction at a concentration of 10 to 20 μM. Further, adenosine was revealed to have a significant action of enhancing the function of tight junction at a concentration of 200 to 400 μM. However, no enhancement action on the function of tight junction was observed in 3'-α-glucosyl adenosine N1-oxide, 5'-α-glucosyl adenosine N1-oxide, adenosine 5'-phosphate, 3'-α-glucosyl adenosine, and 5'-α-glucosyl adenosine at a concentration of 200 to 400 μM.

In the range of the concentrations tested, sodium adenosine N1-oxide 5'-phosphate, adenosine N1-oxide, and adenosine are desirable in terms of effectiveness, among which sodium adenosine N1-oxide 5'-phosphate and adenosine N1-oxide are more desirable. These results indicate that sodium adenosine N1-oxide 5'-phosphate and adenosine N1-oxide are useful as a humectant and an agent for enhancing the skin barrier function, depending on their enhancement actions on the function of tight junction.

Experiment 3: Enhancement Action of Adenosine N1-Oxide 5'-Phosphate on the Expression of Filaggrin Protein in Normal Human Epidermal Keratinocyte Filaggrin is known as a protein that plays an important role in the formation of barrier function and the moisture retention in the skin; it is generated in the epidermis as a profilaggrin which is decomposed into filaggrin that plays a role in barrier function. Filaggrin is successively decomposed to act as a natural humectant factor. The relationship between the expression reduction of filaggrin and atopic dermatitis is recently pointed out in Osawa et al., *Allergology International*, Vol. 60, No. 1, pp. 1 to 9, 2011. In this experiment, sodium adenosine N1-oxide 5'-phosphate was examined for its enhancement action on the expression of filaggrin protein in normal human epidermal keratinocyte, in accordance with the method in Otsuka et al., "*The Journal of Allergy and Clinical Immunology*", Vol. 133, No. 1, pp. 139 to 146, 2014.

Using 6-well culture plates, normal human epidermal keratinocytes, which had been suspended and inoculated to "EpiLife", a product name of a medium containing a growth factor for keratinocytes, commercialized by Kurabo Industries Inc., Osaka, Japan, at a concentration of $5 \times 10^4$ cells/well, were cultured at 37° C. for four days, at which the cells reached a 80% confluent state. Then, the expression of filaggrin was induced in such a manner of further culturing the cells for another four days, while replacing the culture medium with an EpiLife medium supplemented with 2 μM, 5 μM, or 10 μM of sodium adenosine N1-oxide 5'-phosphate every three days. A positive control was provided similarly as above except for using an EpiLife medium supplemented with calcium chloride to give a concentration of 0.5 mM in place of sodium adenosine N1-oxide 5'-phosphate. After four days culture, the resultant cells were washed with Dulbecco's phosphate buffered saline, added with 0.1 mL of an SDS sample buffer (pH 6.8) containing 62.5 mM Tris-HCl, 2% SDS, 10% glycerol, and 50 mM DTT along with a protease inhibitor, and collected with a cell scraper. The collected cells were boiled for 10 min, disrupted ultrasonically, and quantified with "Pierce BCA Protein Assay Kit", commercialized by ThermoFisher Scientific K. K., Yokohama, Japan. A prescribed amount of the resulting disrupted cells was sampled and subjected to SDS-polyacrylamide gel electrophoresis in an amount of 100 μg/lane, and the resulting gel was transferred to a PVDF membrane.

The resulting transferred PVDF membrane was blocked with "Block Ace", commercialized by DS Pharma Biomedical Co., Ltd., Osaka, Japan, reacted with a 200-fold dilution of "AKH1", a mouse anti-filaggrin antibody, commercialized by, Santa Cruz Biotechnology Inc., CA, USA, or a 20,000-fold dilution of "MAB1501", a mouse actin antibody, commercialized by Chemicon International Inc., MA, USA, as a first antibody, and then reacted with a 2,000-fold dilution of "P0447", an HRP-labeled anti-mouse immunoglobulin, commercialized by Dako Japan, Tokyo, Japan, as a secondary antibody. After the reaction, by using ECL Plus Western Blotting Detection System, commercialized by GE Healthcare Japan, Tokyo, Japan, bands were detected on "Hyperfilm ECL", a chemiluminescent film commercialized by GE Healthcare Japan, Tokyo, Japan. The detected bands were analyzed and quantified with "Image J", an image analyzing software.

A control system with no addition of any of the test substances was provided and the increasing intensity ratio of a band of filaggrin/actin was regarded as 100%, with which data for the increased percentages of the intensity ratios of bands of filaggrin/actin of the test substances were comparatively evaluated. Table 5 shows the effect of sodium adenosine N1-oxide 5'-phosphate on the expression of filaggrin protein in normal human epidermal keratinocytes.

TABLE 5

| Test substance | | Relative expression level of filaggrin protein (%) |
|---|---|---|
| Control | | 100 |
| CaCl$_2$ (0.5 mM) | | 289 |
| Sodium adenosine N1-oxide 5'-phosphate | 2 μM | 133 |
| | 5 μM | 206 |
| | 10 μM | 308 |

As clear from Table 5, compared to the control system with no addition of any of the test substance, the test systems with sodium adenosine N1-oxide 5'-phosphate increased the expression level of filagrrin protein in a dose dependent manner, resulting in observing an increment by 308% at 10 μM as equal to that of the positive control with 0.5 mM calcium chloride. These results indicate that the action of enhancing the function of tight junction by sodium adenosine N1-oxide 5'-phosphate is partly made through the action of enhancing the expression of filaggrin protein, meaning that the substance is useful as a humectant and an agent for enhancing the barrier function in the skin.

Recently, it is noted that reduction of skin barrier function causes the invasion of external substances via the skin and results in easily establishing the sensitization to external allergens, which relates to the onset of atopic dermatitis. The experiment result indicates that sodium adenosine N1-oxide 5'-phosphate may lead to the prevention of the onset of atopic dermatitis via the enhancement action by filaggrin protein.

Experiment 4: Effect of the Enhancement Action of Adenosine N1-Oxide 5'-Phosphate Analogues on the Elastin Production of Normal Human Dermal Fibroblasts (NHDF)

Elastin, a fiber having a role in supporting collagen fibers, has a role in imparting tension and elasticity to the skin; the denaturation of elastin reduces the elasticity of the skin and leads to the formation of wrinkles and saggings. Therefore, the enhancement of elastin production prevents or improves wrinkles and saggings. In this experiment, there was examined the effect of adenosine N1-oxide 5'-phosphate and analogues thereof on the production of elastin. The experiment was conducted in accordance with Syedain and Tranquillo, "*Journal of Biomechanics*", Vol. 44, No. 5, pp. 848 to 855, 2011.

Normal human dermal fibroblasts (NHDF), which had been suspended in a Dulbecco's Modified Eagle Medium supplemented with 10% fetal calf serum to give a cell concentration of $3 \times 10^5$ cells/mL, were placed in 24-well plates by 0.5 mL/well and cultured for one day. The cultured cells were washed with Dulbecco's phosphate buffered saline and cultured for another two days in a Dulbecco's Modified Eagle Medium, supplemented with any one of the test substances in Table 5 at respective concentrations shown in the table, to induce elastin synthesis. Thereafter, each culture supernatant was collected, and the remaining cells were washed with one milliliter of Dulbecco's phosphate buffered saline, added with 0.1 mL of 0.25% trypsin and ethylenediaminetetraacetate, followed by incubation at 37° C. for two minutes to detach the cells from the plates. A half milliliter of Dulbecco's phosphate buffered saline was added to each plate, and the resulting cell suspensions were collected in a 1.5-mL tube which was then subjected to centrifugation (3,000×g for five minutes) to collect the cells. Elastin was quantified with a colorimetric determination kit commercialized by Biocolor Ltd., Tokyo, Japan. The previously collected supernatant was used to suspend the collected cells, to which was then added 0.16 mL of 1 M oxalic acid, a reagent affixed to the kit, and incubated at 100° C. for one hour to solubilize elastin. To the solubilized elastin placed in a container was added 0.66 mL of an elastin precipitant as a reagent affixed to the kit, mixed for 15 min while repeatedly reversing the container, and centrifuged at 10,000×g for 10 min to precipitate proteins. A half milliliter of a dye, as a reagent affixed to the kit, was added to the resulting precipitate, followed by repeatedly reversing the container for 90 min and centrifuged at 10,000×g for 10 min to collect sediments bound with the dye. Thereafter, the collected sediments were added with 0.25 mL of a dye separator as a reagent affixed to the kit, and mixed for one hour while repeatedly reversing a container with the resulting mixture, followed by determining the absorbance of the resulting mixture at a wavelength of 490 nm and calculating the amount of elastin per well. A calibration curve was generated with an accessory for the kit. A control system was provided by similarly treating normal human dermal fibroblasts (NHDF) without adding any test substance and determined for its absorbance at a wavelength of 490 nm. Regarding the absorbance as 100%, the production level of elastin of each test substance was comparatively evaluated based on the following equation.

Equation: Production level of elastin (relative value (%))=[(Absorbance of a sample with any one of test substances)/(Absorbance of control)]×100

To confirm cell proliferation under the above conditions tested, normal human dermal fibroblasts (NHDF), which had been suspended in a Dulbecco's Modified Eagle Medium supplemented with 10% fetal calf serum to give a cell concentration of $2.5 \times 10^5$ cells/mL, were placed in 96-well microplates by 0.1 mL/well and cultured for one day. The resulting cells were washed with Dulbecco's phosphate buffered saline and cultured for another two days in a Dulbecco's Modified Eagle Medium supplemented with any one of the test substances in Table 5. The culture supernatants were removed from the microplates, to which were then added 0.2 mL/well of a dilution of "Alamar Blue" diluted with the same culture medium as used in the above by 10 folds to react with the cells at 37° C. for two hours, followed by measuring the fluorescent intensity of the cells at an excitation wavelength of 544 nm and a fluorescent wavelength of 590 nm and obtaining the variation of the number of cells with the addition of any one of the test substances based on the fluorescent intensity of a control system, which had been treated similarly as in the above except for not adding any of the test substances, being regarded as 100%.

The experiment was repeated three times, and the data was compared to that of control with the Dunnett's multiple comparisons test. The symbol "*" means a level of significance of p<0.01. Table 6 shows the action of analogues of adenosine N1-oxide 5'-phosphate on the production of elastin of the normal human dermal fibroblasts (NHDF).

TABLE 6

| Test substance | | Production level of elastin (%) | Number of cells (%) |
|---|---|---|---|
| Control | | 100.0 | 100.0 |
| Sodium adenosine N1-oxide 5'-phosphate | 1 μM | 98.0 | 104.0 |
| | 4 μM | 105.2 | 104.0 |
| | 10 μM | 121.2* | 101.0 |
| Adenosine N1-oxide | 1 μM | 108.8 | 99.0 |
| | 4 μM | 114.8 | 98.0 |
| | 10 μM | 118.4* | 94.0 |
| Adenosine 5'-phosphate | 10 μM | 114.4 | 101.0 |
| | 40 μM | 117.2 | 102.0 |
| | 100 μM | 120.0* | 99.0 |

As clear from Table 6, compared to control with no addition of any test substance, test groups with sodium adenosine N1-oxide 5'-phosphate or adenosine N1-oxide increased in the production level of elastin to about 120% at a concentration of 10 μM, showing a significant enhancement action in the production of elastin. While, adenosine 5'-phosphate tended to enhance the production of elastin at a concentration of 10 to 40 μM, and showed a significant enhancement action in the elastin production at a concentration of 100 μM. No influence of the test substances on cell proliferation was observed in the experiment.

In view of effectiveness, it can be said that, in the range of concentrations tested, sodium adenosine N1-oxide 5'-phosphate, adenosine N1-oxide, and adenosine 5'-phosphate are desirable in the enhancement action of the production of elastin; and sodium adenosine N1-oxide 5'-phosphate and adenosine N1-oxide are more desirable. These results indicate that sodium adenosine N1-oxide 5'-phosphate and its analogue, i.e., adenosine N1-oxide are useful as an anti-wrinkle agent, depending on their actions of enhancing the production of elastin.

Experiment 5: Effect of the Inhibitory Action of Adenosine N1-Oxide 5'-Phosphate and Analogues Thereof on the Matrix Metalloproteinase-1 Production of Normal Human Dermal Fibroblasts (NHDF)

It is said that the hydrolysis of collagen by matrix metalloproteinase-1 induces the formation of wrinkles and the reduction of elasticity in the skin to cause saggings; the inhibition of the production of matrix metalloproteinase-1 would prevent or improve such wrinkles and saggings. The experiment was demonstrated to examine the effect of adenosine N1-oxide 5'-phosphate and analogues thereof on the production of matrix metalloprotease-1, in accordance with the procedure disclosed in Fuller et al., "*Journal of Cosmetic Dermatology*", Vol. 5, No. 1, pp. 30 to 38, 2006"

Normal human dermal fibroblasts (NHDF), which had been suspended in a Dulbecco's Modified Eagle Medium supplemented with 10% fetal calf serum to give a concentration of $2.5 \times 10^5$ cells/mL, were placed in 96-well microplates by 0.1 mL/well and cultured until reaching a confluent state over the bottom of each well. Thereafter, the medium in each well was replaced with a fresh serum-free culture medium and culture for another 24 hours, added with any one of the test substances in Table 6 at each concentration shown in the table, and cultured for additional 24 hours. Then, the resulting cell cultures were added with human IL-1β to give a final concentration of 1 ng/ml, followed by culturing the cells for another 24 hours. After completion of the culture, matrix metalloprotease-1 in the supernatant in each well was detected with an enzyme-linked immuno sorbent assay (ELISA), commercialized by R & D Systems, Inc., MN, USA, developed coloration with tetramethylbenzidine, and measured for absorption at a wavelength of 450 nm. A control system was provided similarly as above except for not adding any test substance, and determined for the activity of matrix metalloprotease-1 similarly as in the above to be regarded as 100%. The production level of matrix metalloprotease-1 for each test substance was comparatively evaluated based on the following equation.

Equation: Production level of matrix metalloprotease-1 (relative value (%))=[(Absorbance of a sample with any one of test substances)/(Absorbance of control)]×100

The number of cells was counted with a cytometry kit (or a staining method) and the variation of cell number when added with any one of the test substances, based on the value of control being regarded as 100%.

The experiment was repeated three times, and the data were compared to that of control with the Dunnett's multiple comparisons test. The symbol "*" means a level of significance of $p<0.01$. Table 7 shows the action of analogues of adenosine N1-oxide 5'-phosphate on the production of matrix metalloprotease-1.

| Test substance | | Production level of matrix metalloprotease-1 (%) | Number of cells (%) |
|---|---|---|---|
| Control | | 100.0 | 100.0 |
| Sodium adenosine | 5 μM | 96.0 | 99.9 |
| N1-oxide 5'-phosphate | 10 μM | 83.1* | 99.5 |
| | 20 μM | 31.8* | 92.2 |
| Adenosine N1-oxide | 5 μM | 86.6 | 98.5 |
| | 10 μM | 77.6* | 94.6 |
| | 20 μM | 31.9* | 94.4 |
| 3'-α-Glucosyladenosine N1-oxide | 200 μM | 78.7* | 103.8 |
| | 400 μM | 75.5* | 104.5 |
| | 800 μM | 68.6* | 97.4 |
| 5'-α-Glucosyladenosine N1-oxide | 200 μM | 85.4* | 108.1 |
| | 400 μM | 83.6* | 102.1 |
| | 800 μM | 77.0* | 102.6 |
| Adenosine | 200 μM | 88.7 | 93.5 |
| | 400 μM | 93.4 | 87.4 |
| | 800 μM | 85.6 | 91.2 |
| Adenosine 5'-phosphate | 200 μM | 99.5 | 93.7 |
| | 400 μM | 93.3 | 89.9 |
| | 800 μM | 90.3 | 96.0 |
| 3'-α-Glucosyladenosine | 200 μM | 86.6 | 98.9 |
| | 400 μM | 87.1 | 101.1 |
| | 800 μM | 98.7 | 107.2 |
| 5'-α-Glucosyladenosine | 200 μM | 89.9 | 104.0 |
| | 400 μM | 94.3 | 103.4 |
| | 800 μM | 87.7 | 93.4 |

As clear from Table 7, compared to a control system without adding any test substance, a test system with sodium adenosine N1-oxide 5'-phosphate reduced its production level of matrix metalloprotease-1 to a level of about 80 to about 30% at a concentration of 10 to 20 μM and showed a dose-dependent and significant production inhibitory action. In a test system with adenosine N1-oxide, a similar production inhibitory action was observed at a concentration of 5 to 20 μM. In the systems with 3'-α-glucosyladenosine N1-oxide and 5'-α-glucosyladenosine N1-oxide showed a dose-dependent and significant production inhibitory action at a concentration of 200 to 800 μM, wherein the inhibitory action by 3'-α-glucosyl adenosine N1-oxide was stronger than that of 5'-α-glucosyl adenosine N1-oxide. There was not observed any significant matrix metalloprotease-1 production inhibitory action by adenosine, adenosine, adenosine 5'-phosphate, 3'-α-glucosyladenosine N1-oxide, and 5'-α-glucosyladenosine.

Within the range of concentrations tested, sodium adenosine N1-oxide 5'-phosphate, adenosine N1-oxide, 3'-α-glucosyl adenosine N1-oxide, and 5'-α-glucosyl adenosine N1-oxide are preferable in terms of effectiveness on matrix metalloprotease-1 inhibitory action, and among which sodium adenosine N1-oxide 5'-phosphate and adenosine N1-oxide are more preferable. These results indicate that adenosine N1-oxide 5'-phosphate, analogues thereof, and their salts are useful as anti-wrinkle agents, depending on their matrix metalloprotease-1 inhibitory actions.

Experiment 6: Effect of the Inhibitory Action of Adenosine N1-Oxide 5'-Phosphate and Analogues Thereof on the Endothelin-1 Production of Normal Human Epidermal Keratinocyte It is known that endothelin-1 is a substance that enhances the activation and proliferation of melanocyte and causes spots. It is also noticed that skin pigmentation/spot or skin dullness may be induced when melanin, secreted from melanocytes to epidermal cells, is not smoothly eliminated from epidermal cells. Accordingly, the inhibition of endothelin-1 would prevent or improve skin pigmentation/spot and skin dullness. Therefore, in this experiment, the effect of adenosine N1-oxide 5'-phosphate and analogues thereof on the production of endothelin-1. This experiment was made in accordance with Ishida and Sakaguchi, "*Biological & Pharmaceutical Bulletin*", Vol. 30, No. 5, pp. 928 to 934, 2007.

Normal human epidermal keratinocytes were proliferated to a confluent state at which the cells were grown over the entire bottom edge of each well of 96-well microplates by using "EpiLife", a product name of a culture medium containing a growth factor for keratinocytes, commercialized by Life Technologies Corporation, CA, USA, and further cultured for another two days while replacing the medium with a fresh culture medium free of such a growth factor. Thereafter, the resulting cultures were added with sodium adenosine N1-oxide 5'-phosphate to give a concentration of 10, 20, or 50 μM, and allowed to stand for six hours. The cultured cells were washed with Hanks buffer, irradiated with ultraviolet B radiation at an intensity of 40 mJ/cm$^2$, and further cultured for 24 hours after the addition of a culture medium containing the growth factor. Endothelin-1 in the resulting supernatants was detected with an endothelin-1 specific ELISA kit, commercialized by R&D Systems Inc., MN, USA, colored with tetramethylbenzidine, and measured for absorbance at a wavelength of 450 nm. A control system was provided and similarly treated as above except for not adding sodium adenosine N1-oxide 5'-phosphate and then determined for the production level of endothelin-1 in the resulting culture supernatant to be regarded as 100%. The production level of endothelin-1 for each test substance was comparatively evaluated based on the following equation.

Equation: Production level of endothelin-1 (relative value (%))=[(Absorbance of a sample with a test substance)/(Absorbance of control)]×100

The number of proliferated cells was determined with methylene blue and regarded as 100% for use in calculating the variation of cells with any one of the test substances.

The experiment was repeated three times, and the data was compared to that of control with the Dunnett's multiple comparisons test. The symbol "*" means a level of significance of p<0.01. Table 8 shows the action of sodium adenosine N1-oxide 5'-phosphate on the production level of endothelin-1 by normal human epidermal keratinocytes.

TABLE 8

| Test substance | | Production level of endothelin-1 (%) | Number of cells (%) |
|---|---|---|---|
| Control | | 100.0 | 100.0 |
| Sodium adenosine N1-oxide 5'-phosphate | 10 μM | 104.5 | 111.4 |
| | 20 μM | 87.9 | 103.6 |
| | 50 μM | 49.9* | 100.6 |

As clear from Table 8, compared to the control system without addition of any test substance, the test system with sodium adenosine N1-oxide 5'-phosphate tended to show a production inhibition of endothlin-1 at a concentration of 20 μM and gave a production level of endothelin-1 reduced by about 50% at a concentration of 50 μM, revealing that it has a significant endothelin-1 production inhibitory action. No influence on cell proliferation was found in the experimental system.

The above result indicates that adenosine N1-oxide 5'-phosphate is useful as an agent for anti-spots, depending on its endothelin-1 production inhibitory action.

Experiment 7: Effect of the Combination Use of Epigallocatechin Gallate and Adenosine N1-Oxide 5'-Phosphate on the Induction of Differentiating Keratinocytes Except for adding the test substances listed in Tables 8 and 9 at respective concentrations shown in the tables, experiments were respectively conducted in accordance with the methods in Experiments 1-2 and 1-3 disclosed in the specification to examine the effect of the combination use of epigallocatechin gallate, which is used as an antioxidant for cosmetics, and sodium adenosine N1-oxide 5'-phosphate on the action of accelerating the cornified-envelope production and the action of enhancing the transglutaminase activity of sodium adenosine N1-oxide 5'-phosphate. A control system was provided and similarly treated as above except for not adding any test substance and was determined for both the increase rates of cornified-envelope production level and the transglutaminase activity, based on the following equations.

Equation: Increase rate of cornified envelope production level (%)={[(Absorbance of a sample with any one of test substances)/(Absorbance of control)]×100}−100

Equation: Increase rate of transglutaminase (%)={[(Absorbance of a sample with any one of test substances)/(Absorbance of control)]×100}−100

Respective results are in Tables 9 and 10, where the symbol "*" is affixed to an increase rate as an effective combination.

TABLE 9

| Test substance | | Increase rate of cornified envelope formation level (%) |
|---|---|---|
| Sodium adenosine N1-oxide 5'-phosphate | 15 μM | 2.8 |
| Epigallocatechin gallate | 1.6 μM | 28.0 |
| | 3.3 μM | 37.3 |
| Epigallocatechin gallate + 15 μM Sodium adenosine N1-oxide 5'-phosphate | 1.6 μM | 43.1* |
| | 3.3 μM | 59.2* |

TABLE 10

| Test substance | | Increase rate of transglutaminase activity (%) |
|---|---|---|
| Sodium adenosine N1-oxide 5'-phosphate | 15 μM | 0.0 |
| Epigallocatechin gallate | 1.6 μM | 5.6 |
| | 3.3 μM | 19.0 |
| | 6.5 μM | 6.5 |
| Epigallocatechin gallate + 15 μM Sodium adenosine N1-oxide 5'-phosphate | 1.6 μM | 73.2* |
| | 3.3 μM | 109.8* |
| | 6.5 μM | 99.2* |

As clear from Tables 9 and 10, the combination use of 15 μM of sodium adenosine N1-oxide 5'-phosphate and 1.6 to 6.5 μM of epigallocatechin gallate distinctly improved both the increase rates of cornified envelope production level and transglutaminase activity compared to the case with a single use of sodium adenosine N1-oxide 5'-phosphate or epigallocatechin gallate. Based on these results, the combination use of sodium adenosine N1-oxide 5'-phosphate and epigallocatechin gallate was judged to have a synergistic effect on both the action of accelerating the production of cornified envelope and the action of enhancing the transglutaminase activity. A preferable molar ratio of sodium adenosine N1-oxide 5'-phosphate to epigallocatechin gallate is in the range of from 15 μM:6.5 μM to 15 μM:1.6 μM, i.e., 2.3:1 to 9.4:1. Since these results indicate that compositions with any of adenosine N1-oxide 5'-phosphate, analogues thereof, and their salts incorporated with epigallocatechin gallate synergistically accelerate or enhance the production of cornified envelope and the glutaminase activity, such compositions are useful as anti-wrinkle agents.

Experiment 8: Effect of the Combination Use of Adenosine N1-Oxide 5'-Phosphate and Ethylenediaminetetraacetate on the Function of Tight Junction Except for adding the test substances listed in Table 11 at respective concentrations shown in the table, experiments were respectively conducted in accordance with the methods in Experiment 2 disclosed in the specification to examine the effect of the combination use with ethylenediaminetetraacetate used as a preservative for cosmetics on the action of reinforcing the function of tight junction by sodium adenosine N1-oxide 5'-phosphate. A control system was provided and similarly treated as above except for not adding any test substance. The reduction rate of relative transmittance of lucifer yellow against that of control based on the following equation.

Equation: Reduction rate of relative transmittance of lucifer yellow (%)=100−[(Transmittance of a sample with any one of test substances)/(Transmittance of control)]×100

The results are in Table 11, where the symbol "*" is affixed to a reduction rate for an effective combination.

TABLE 11

| Test substance | Reduction rate of relative transmittance of lucifer yellow (%) |
|---|---|
| 10 μM Sodium adenosine N1-oxide 5'-phosphate | 21.6 |
| 3 mM Ethylenediaminetetraacetate | −24.7 |
| 3 mM Ethylenediaminetetraacetate + 10 μM Sodium adenosine N1-oxide 5'-phosphate | 17.0* |

As clear from Table 11, ethylenediaminetetraacetate usable as a preservative for cosmetics exhibited per se an action of depressing the function of tight junction, however, it was observed that the degree of such depression is moderated by a large margin when used in combination with sodium adenosine N1-oxide 5'-phosphate. The above results also indicate that, whenever adenosine N1-oxide 5'-phosphate and ethylenediaminetetraacetate are used in a molar ratio of at least 10 μM:3 mM, i.e., at least 1:300, a sufficient level of enhancement in the function of tight junction can be attained by using adenosine N1-oxide 5'-phosphate, even in the presence of ethylenediaminetetraacetate. Further, the results show that compositions with ethylenediaminetetraacetate together with any of adenosine N1-oxide 5'-phosphate, analogues thereof, and their salts are useful as agents for moisturizing the skin and enhancing the skin barrier function.

Experiment 9: Effect of the Combination Use of Ascorbic Acid 2-Glucoside and Adenosine N1-Oxide 5'-Phosphate or any of Analogues Thereof on the Production of Matrix Metalloprotease-1

Except for adding the test substances listed in Table 12 at respective concentrations shown in the table, experiments were respectively conducted in accordance with the methods in Experiment 5 disclosed in the specification to examine the effect of the combination use with ascorbic acid 2-glucoside used as a skin whitener in cosmetics on the action of anti-wrinkles by analogues of adenosine N1-oxide 5'-phosphate. A control system was provided and similarly treated as above except for not adding any test substance. The reduction rate of the production level of matrix metalloprotease-1 against that of control based on the following equation.

Equation: Reduction rate of the production level of matrix metalloprotease-1(%)=100−[(Absorbance of a sample with any one of test substances)/(Absorbance of control)]×100

The results are in Table 12, where the symbol "*" is affixed to a reduction rate for an effective combination.

TABLE 12

| Test substance | | Reduction rate of the production level of matrix metalloprotease-1 activity (%) |
|---|---|---|
| Ascorbic acid 2-glucoside | 200 μM | 2.1 |
| Sodium adenosine N1-oxide 5'-phosphate | 2 μM | 2.9 |
| | 5 μM | 4.0 |
| | 10 μM | 16.9 |
| Sodium adenosine N1-oxide 5'-phosphate plus 200 μM of Ascorbic acid 2-glucoside | 2 μM | 6.7 |
| | 5 μM | 13.0* |
| | 10 μM | 24.7* |
| Adenosine N1-oxide | 2 μM | 10.0 |
| | 5 μM | 13.4 |
| | 10 μM | 22.4 |
| Adenosine N1-oxide + 200 μM Ascorbic acid 2-glucoside | 2 μM | 11.3 |
| | 5 μM | 24.4* |
| | 10 μM | 36.3* |

As clear from Table 12, the combination use of 5 to 10 μM of sodium adenosine N1-oxide 5'-phosphate or adenosine N1-oxide as an analogue thereof 200 μM of ascorbic acid 2-glucoside distinctly increased in the reduction rate of the production level of matrix metalloprotease-1 compared to the mere sum of those of their respective single-use. For this reason, the combination use of sodium adenosine N1-oxide 5'-phosphate or adenosine N1-oxide and ascorbic acid 2-glucoside was judged to have a synergistic effect on the production inhibitory action of matrix metalloprotease-1. The preferable molar ratio of adenosine N1-oxide 5'-phosphate and ascorbic acid 2-glucoside is ranging from 5 μM:200 μM to 10 μM:200 μM, i.e., 1:40 to 1:20. The results indicate that compositions containing any of adenosine N-oxide 5'-phosphate, analogues thereof, and their salts in combination with ascorbic acid 2-glucoside are useful as agents for anti-wrinkles because they synergistically inhibit the production of matrix metalloprotease-1.

Experiment 10: Effect of Light on Adenosine N1-Oxide 5'-Phosphate and Analogues Thereof Since external dermal agents may be exposed to light upon use, any effective ingredients contained therein should desirably be non-phototoxic and photostable. The meaning of phototoxic is a phenomenon where, when any chemical substances or mixtures thereof are administered to subjects and then exposed to light, the administered substances react with the light to induce disorders in cells of the skin. In this experiment, photostability of adenosine N1-oxide 5'-phosphate and analogues thereof such as adenosine N1-oxide and 5'-glucosyl adenosine N1-oxide were measured for comparison.

To 25 mg of each of the test substances in Table 13 was added each of McIlvain buffers adjusted to different pHs to give a total volume of 50 mL and distributed to transparent glass screw bottles (5 mL) with plastic screw caps equal to the number of the test substances by 2.0 mL. Under a fluorescent lamp with about 4,000 lux at 28° C., the glass screw bottles were allowed to lay along. Sodium adenosine N1-oxide 5'-phosphate and 5'-glucosyl adenosine N1-oxide were respectively analyzed on HPLC at the initiation of the test and at eight weeks after initiating the experiment, and at the initiation of the test and at two weeks intervals up to eight weeks after the initiation, followed by taking out one of the bottles for HPLC analysis. The analysis was repeated three times and the average residual percentage of each test substance was calculated based on the area ratio against the peak area for each test substance upon HPLC chromatogram at the initiation of the experiment. Table 13 shows the optical tolerance of adenosine N1-oxide 5'-phosphate and analogues thereof.

Equation: Residual percentage (%) of test substance=[(Average peak area after a prescribed time lapse at respective pHs for each test substance)/(Average peak area at the initiation of experiment at respective pHs for each test substance)]×100

| Test substance | pH | Residual percentage (%) | | | | |
|---|---|---|---|---|---|---|
| | | At the initiation of experiment | Two weeks | Four weeks | Six weeks | Eight weeks |
| Sodium adenosine N1-oxide 5'-phosphate | 4 to 5 | 100.0 | | | | 93.0 |
| | 6 to 7 | 100.0 | | | | 88.8 |
| | 8 to 9 | 100.0 | | | | 96.9 |
| Adenosine N1-oxide | 4 to 5 | 100.0 | 68.8 | 47.2 | 25.2 | 24.6 |
| | 6 to 7 | 100.0 | 90.6 | 81.6 | 71.3 | 66.2 |
| | 8 to 9 | 100.0 | 83.7 | 77.2 | 68.2 | 63.1 |
| 5'-α-Glucosyl adenosine N1-oxide | 4 to 5 | 100.0 | 51.7 | 27.3 | 9.7 | 9.8 |
| | 6 to 7 | 100.0 | 79.1 | 57.7 | 40.8 | 34.3 |
| | 8 to 9 | 100.0 | 70.7 | 47.8 | 35.4 | 24.0 |

As clear from Table 13, sodium adenosine N1-oxide 5'-phosphate was distinctly stable against light because it showed a residual percentage of about 89 to 97% under the pH conditions of 4 to 9 at eight weeks after initiating the experiment. On the contrary, adenosine N1-oxide was unstable against light because it showed residual percentages of about 63 to 66% and about 25% under respective pH conditions of 6 to 9 and of 4 to 5 at eight weeks after initiating the experiment. Further, 5'-glucosyl adenosine N1-oxide was distinctly unstable against light because it showed residual percentages of about 24 to 34% and about 10% under respective pH conditions of 6 to 9 and of 4 to 5 at eight weeks after initiating the experiment.

The aforesaid results show that sodium adenosine N1-oxide 5'-phosphate is more stable against light under different pH conditions compared to analogues thereof, indicating that adenosine N1-oxide 5'-phosphate is more advantageously used as an effective ingredient for external dermal agents in view of that such analogues of sodium adenosine N1-oxide 5'-phosphate are more susceptible to easily decompose under the exposure of sunlight compared to that of fluorescent light.

An experiment, conducted in accordance with "TG432: In vitro 3T3 NRU Phototoxicity Test" as an OECD test guideline that is an internationally-agreed experimental method for evaluating safeness of chemical substances and mixtures thereof, there was found no optical toxicity sodium adenosine N1-oxide 5'-phosphate, adenosine N1-oxide, 3'-α-glucosyl adenosine N1-oxide, and 5'-glucosyl adenosine N1-oxide. Based on this, external dermal agent containing any of adenosine N1-oxide 5'-phosphate, analogues thereof, and their salts can be said to be safe.

The present invention is explained in more detail with reference to the following Examples, however, they should never restrict the scope of the present invention.

Example 1

<Cosmetic Lotion>
(Composition)

| | Ingredients | (% by mass) |
|---|---|---|
| (1) | Glycerin | 4.0 |
| (2) | Propylene glycol | 3.0 |
| (3) | 1,2-Pentanediol | 0.1 |
| (4) | Sodium adenosine N1-oxide 5'-phosphate | 1.0 |
| (5) | Polyoxyethylene (20) oleyl alcohol | 0.5 |
| (6) | Strawberry geranium extract | 2.0 |
| (7) | Ethanol | 5.0 |
| (8) | Flavor | q.s. |
| (9) | Refined water | Balance |

The above ingredients (1) to (4) were dissolved in the ingredient (9), and the resulting solution was admixed with a mixture, which had been prepared by mixing the ingredients (5) to (8), to prepare a cosmetic lotion. Since the product contains sodium adenosine N1-oxide 5'-phosphate, it is an improved cosmetic lotion capable of enhancing the skin turnover and useful as the one for anti-ageing that has an advantageous action of maintaining or enhancing the skin barrier function and the production of elastin, as well as having an improved action of anti-wrinkles, anti-fine wrinkles, anti-saggings, and anti-spots. Also, it is a cosmetic lotion with an improved antiseptic effect and moisture retainability because it contains 1,2-pentane diol.

Example 2

<Milky Lotion>
(Composition)

| | Ingredients | (% by mass) |
|---|---|---|
| (1) | 1,2-Hexanediol | 5.0 |
| (2) | Octyldodecanol | 4.0 |
| (3) | Sodium adenosine N1-oxide 5'-phosphate | 0.1 |
| (4) | "AA2G", a product name of ascorbic acid 2-glucoside commercialized by Hayashibara Co., Ltd., Okayama, Japan | 2.0 |
| (5) | Polyoxyethylene (20) oleyl ether | 1.0 |
| (6) | Stearic acid | 0.5 |
| (7) | Shea butter | 2.0 |
| (8) | Bees wax | 4.0 |
| (9) | p-Hydroxybenzoate ester | 0.2 |
| (10) | Marmelo seed extract | 5.0 |
| (11) | Xanthane gum | 0.1 |
| (12) | Phytic acid | 0.02 |
| (13) | Vitamin E | 0.01 |
| (14) | Refined water | Balance |

The above ingredients (1), (3), (10), (11), and (14) were mixed into a water phase. While, the ingredients (2), (5) to (9), (12), and (13) were heated and mixed into an oil phase. The water phase was added to the oil phase and mixed to homogeneity, and then cooled, followed by adding the remaining ingredient (4) to the resulting mixture to obtain a milky lotion. Since the product as a milky lotion contains sodium adenosine N1-oxide 5'-phosphate and ascorbic acid 2-glucoside, it is a milky lotion capable of accelerating the skin turnover and it can be advantageously used as the one for anti-ageing that has an advantageous action of maintaining or enhancing the skin barrier function and the production of elastin, as well as having an improved action of anti-wrinkles, anti-fine wrinkles, anti-saggings, and anti-spots.

Example 3

<Cosmetic Milky Lotion>
(Composition)

|   | Ingredients | (% by mass) |
| --- | --- | --- |
| (1) | Stearic acid | 2.5 |
| (2) | Cetanol | 1.5 |
| (3) | Petrolatum | 5.0 |
| (4) | White mineral oil | 10.0 |
| (5) | Polyoxyethylene oleate | 2.0 |
| (6) | Tocopheryl acetate | 0.5 |
| (7) | Glycyrrhizinate dipotassium | 0.2 |
| (8) | Polyethylene glycol 1500 | 3.0 |
| (9) | Sodium adenosine N1-oxide 5'-phosphate | 0.1 |
| (10) | Epigallocatechin gallate | 0.5 |
| (11) | 1,2-Hexanediol | 0.1 |
| (12) | Refined water | Balance |

According to the above formulation, all the ingredients were mixed in usual manner and further admixed with an adequate amount of a flavor to prepare a milky lotion. Since the product contains sodium adenosine N1-oxide 5'-phosphate and epigallocatechin gallate, it is a milky lotion capable of accelerating the skin turnover and it can be advantageously used for anti-ageing that has an advantageous action of maintaining or enhancing the skin barrier function and the production of elastin, as well as having an improved action of anti-wrinkles, anti-fine wrinkles, anti-saggings, and anti-spots.

Example 4

<Cosmetic Cream>
(Composition)

|   | Ingredients | (% by mass) |
| --- | --- | --- |
| (1) | Stearic acid | 5.0 |
| (2) | Cetyl alcohol | 5.0 |
| (3) | Squalane | 8.0 |
| (4) | Petrolatum | 3.0 |
| (5) | Glycerol tri (2-ethylhexanoate) | 7.0 |
| (6) | Dipropylene glycol | 6.0 |
| (7) | Glycerine | 4.0 |
| (8) | Sodium adenosine N1-oxide 5'-phosphate | 0.1 |
| (9) | Edetate disodium | 0.01 |
| (10) | Propylene glycol monostearate | 3.0 |
| (11) | Polyoxyethylene (20) cetyl alcohol ether | 3.0 |
| (12) | 1,2-Hexanediol | 0.2 |
| (13) | Flavor | q.s. |
| (14) | Refined water | Balance |

The ingredients (6) to (9) were added to the ingredient (14), followed by heating the mixture at 60° C. to prepare a water phase. While, the remaining ingredients (1) to (5) and (10) to (13) were mixed and heated to 70° C. to obtain an oil phase, which was then added to the water phase. The mixture thus obtained was emulsified in usual manner into a cream. Since the product is incorporated with sodium adenosine N1-oxide 5'-phosphate, it is an improved cream capable of accelerating the skin turnover and having a satisfactory stability because it contains edetate disodium (or ethylenediaminetetraacetic acid disodium salt). The product is useful as an anti-ageing cosmetic cream that has no sticky feeling but has a satisfactory availability and an advantageous action of maintaining or enhancing the skin barrier function and the production of elastin, as well as having an improved action of anti-wrinkles, anti-fine wrinkles, anti-saggings, and anti-spots.

Example 5

<Serum>
(Composition)

|   | Ingredients | (% by mass) |
| --- | --- | --- |
| (1) | Maltitol | 7.5 |
| (2) | "AA2G", a product name of ascorbic acid 2-glucoside, commercialized by Hayashibara Co., Ltd., Okayama, Japan | 2.0 |
| (3) | 1,2-Alkanediol | 5.0 |
| (4) | Polyethylene glycol 1500 | 1.0 |
| (5) | Ethanol | 5.0 |
| (6) | Carboxyvinyl polymer | 0.4 |
| (7) | Sodium polyacrylate | 0.1 |
| (8) | Polyoxyethylene (20) oleyl ether | 1.5 |
| (9) | Olive oil | 0.2 |
| (10) | Sodium adenosine N1-oxide 5'-phosphate | 0.1 |
| (11) | Potassium hydroxide | q.s. |
| (12) | Flavor | q.s. |
| (13) | Refined water | Balance |

According to the above formulation, all the ingredients were mixed in usual manner to prepare a serum. Since the product is incorporated with sodium adenosine N1-oxide 5'-phosphate, it is a serum capable of accelerating the skin turnover and useful as an anti-ageing serum that has no sticky feeling but has a satisfactory availability and an advantageous action of maintaining or enhancing the skin barrier function and the production of elastin, as well as having an improved action of anti-wrinkles, anti-fine wrinkles, anti-saggings, and anti-spots.

INDUSTRIAL APPLICABILITY

As described above, the anti-ageing external dermal agent of the present invention effectively prevents or improves age-related wrinkles, fine wrinkles, saggings, spots, etc., in the skin because the agent improves the skin turnover, maintains or enhances the skin barrier function and the expression of filaggrin protein in the skin, maintains or accelerates the elastin production in the skin, inhibits the matrix metalloprotease-1 in the skin, or inhibits the endotherin-1 production in the skin. The present invention is a distinctly significant invention that will greatly contribute to the art.

The invention claimed is:
1. An external dermal agent for anti-ageing, which comprises as effective ingredients (i) one or more members selected from the group consisting of adenosine N1-oxide 5'-phosphate, analogues thereof, and their salts; and (ii) ascorbic acid 2-glucoside and/or ethylenediaminetetraacetic acid wherein the molar ratio of said one or more members selected from the group consisting of adenosine N1-oxide

5'-phosphate, analogues thereof, and their salts to said ascorbic acid 2-glucoside is in the range of 1:40 to 1:2, and
wherein the molar ratio of said one or more members selected from the group consisting of adenosine N1-oxide 5'-phosphate, analogues thereof, and their salts to said ethylenediaminetetraacetic acid is at least 1:300.

2. The external dermal agent of claim 1, wherein said analogue(s) of adenosine N1-oxide 5'-phosphate is/are one or more members selected from the group consisting of adenosine N1-oxide, 3'-α-glucosyladenosine N1-oxide, and 5'-α-glucosyladenosine N1-oxide.

3. A method for exerting anti-ageing effect in a subject in need thereof, comprising administering to the subject one or more members selected from the group consisting of adenosine N1-oxide 5'-phosphate, analogues thereof, and their salts, in combination with ascorbic acid 2-glucoside and/or ethylenediaminetetraacetic acid, wherein the molar ratio of said one or more members selected from the group consisting of adenosine N1-oxide 5'-phosphate, analogues thereof, and their salts to said ascorbic acid 2-glucoside is in the range of 1:40 to 1:2, and
wherein the molar ratio of said one or more members selected from the group consisting of adenosine N1-oxide 5'-phosphate, analogues thereof, and their salts to said ethylenediaminetetraacetic acid is at least 1:300.

4. The method of claim 3, wherein said analogue(s) of adenosine N1-oxide 5'-phosphate is/are one or more members selected from the group consisting of adenosine N1-oxide, 3'-α-glucosyladenosine N1-oxide, and 5'-α-glucosyladenosine N1-oxide.

5. The method of claim 3, wherein said anti-ageing effect is one selected from the group consisting of effects for improving skin turnover, for enhancing skin barrier function, for preventing/improving anti-wrinkle, and for preventing/improving anti-spot.

* * * * *